US011813432B2

(12) United States Patent
Farina et al.

(10) Patent No.: US 11,813,432 B2
(45) Date of Patent: *Nov. 14, 2023

(54) METHOD AND APPARATUS FOR THE FAIL-SAFE TERMINATION OF IN VIVO DRUG DELIVERY FROM AN IMPLANTABLE DRUG DELIVERY SYSTEM

(71) Applicant: The Methodist Hospital, Houston, TX (US)

(72) Inventors: Marco Farina, Houston, TX (US); Robert Lyle Hood, Houston, TX (US); Alessandro Grattoni, Houston, TX (US)

(73) Assignee: The Methodist Hospital, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/209,919

(22) Filed: Mar. 23, 2021

(65) Prior Publication Data

US 2022/0040406 A1    Feb. 10, 2022

Related U.S. Application Data

(63) Continuation of application No. 15/769,401, filed as application No. PCT/US2016/057628 on Oct. 19, 2016, now Pat. No. 10,953,154.

(Continued)

(51) Int. Cl.
*A61M 5/168* (2006.01)
*F16K 17/38* (2006.01)
(Continued)

(52) U.S. Cl.
CPC ....... *A61M 5/16881* (2013.01); *A61K 9/0009* (2013.01); *A61K 9/0024* (2013.01);
(Continued)

(58) Field of Classification Search
CPC .............. A61K 9/0009; A61K 9/0024; A61M 5/16881; F16K 17/383; F16K 99/003
See application file for complete search history.

(56) References Cited

U.S. PATENT DOCUMENTS

| 4,952,262 A * | 8/1990 | Washkewicz ........ B29D 23/001 156/149 |
| 2008/0133001 A1 * | 6/2008 | Shalev .................... A61L 31/04 523/112 |

(Continued)

OTHER PUBLICATIONS

"Body temperature norms", MedlinePlus, https://medlineplus.gov/ency/article/001982.htm (Year: 2020).*

(Continued)

*Primary Examiner* — Katherine H Schwiker
*Assistant Examiner* — Rachel T. Smith
(74) *Attorney, Agent, or Firm* — Womble Bond Dickinson (US) LLP

(57) ABSTRACT

A method for the fail-safe termination of in vivo drug delivery from an implantable drug delivery system, the method comprising: providing an implantable drug delivery system comprising: a housing having a reservoir for containing a drug, and a port for dispensing the drug to a patient; and an emergency deactivation unit disposed between the reservoir and the port, the emergency deactivation unit comprising a composite structure comprising a biocompatible ferromagnetic mesh open to fluid flow and a hydrophobic meltable material, the hydrophobic meltable material comprising at least one hole therein for enabling a fluid to pass through the hydrophobic meltable material; implanting the implantable drug delivery system within a patient; enabling the drug to flow from the reservoir, through the at least one hole in the hydrophobic meltable material and out the port; and when drug flow is to be terminated, applying a magnetic field to the composite structure, such that a (Continued)

Exploded schematic of nDS capsule with PCL+mesh composite layer current is induced in the ferromagnetic mesh which heats the ferromagnetic mesh and melts the hydrophobic meltable material, thereby closing the at least one hole in the hydrophobic meltable material and blocking drug delivery to the patient.

17 Claims, 14 Drawing Sheets

Related U.S. Application Data

(60) Provisional application No. 62/243,265, filed on Oct. 19, 2015.

(51) Int. Cl.
*F16K 13/10* (2006.01)
*F16K 99/00* (2006.01)
*A61K 9/00* (2006.01)
*A61K 47/02* (2006.01)
*A61K 47/34* (2017.01)
*A61M 5/142* (2006.01)
*A61M 5/14* (2006.01)

(52) U.S. Cl.
CPC .............. *A61K 47/02* (2013.01); *A61K 47/34* (2013.01); *A61M 5/14276* (2013.01); *F16K 13/10* (2013.01); *F16K 17/38* (2013.01); *F16K 99/003* (2013.01); *F16K 99/0044* (2013.01); *A61M 5/14* (2013.01); *A61M 2205/02* (2013.01); *A61M 2205/0288* (2013.01); *A61M 2205/3523* (2013.01); *A61M 2207/00* (2013.01); *F16K 2099/0088* (2013.01)

(56) References Cited

U.S. PATENT DOCUMENTS

| | | | | |
|---|---|---|---|---|
| 2010/0152699 | A1* | 6/2010 | Ferrari | B82Y 5/00 216/37 |
| 2011/0123398 | A1* | 5/2011 | Carrilho | F16K 99/0001 422/68.1 |
| 2014/0283863 | A1* | 9/2014 | Krenke | A47K 7/03 132/200 |
| 2017/0314695 | A1* | 11/2017 | Hathaway | F16K 31/002 |

OTHER PUBLICATIONS

"Polycaprolactone", ScienceDirect, https://www.sciencedirect.com/topics/chemical-engineering/polycaprolactone (Year: 2012).*

Sidambe, Biocompatibility of Advanced Manufactured Titanium Implants—A Review, 2014, Materials (Basel) 2014, 7(12); 8168-8188 (Year: 2014).*

* cited by examiner

Section of assembled nDS capsule with composite layers.

Exploded schematic of nDS capsule with PCL+mesh composite layer

Approach: a) assembly of the composite layer inside the PEEK cap; b) polymer surface modification with NaOH to increase it's wettability; c) assembling of the whole PEEK Capsule; d) application of the magnetic field to close holes.

Normalized release data showing deactivation of drug release.

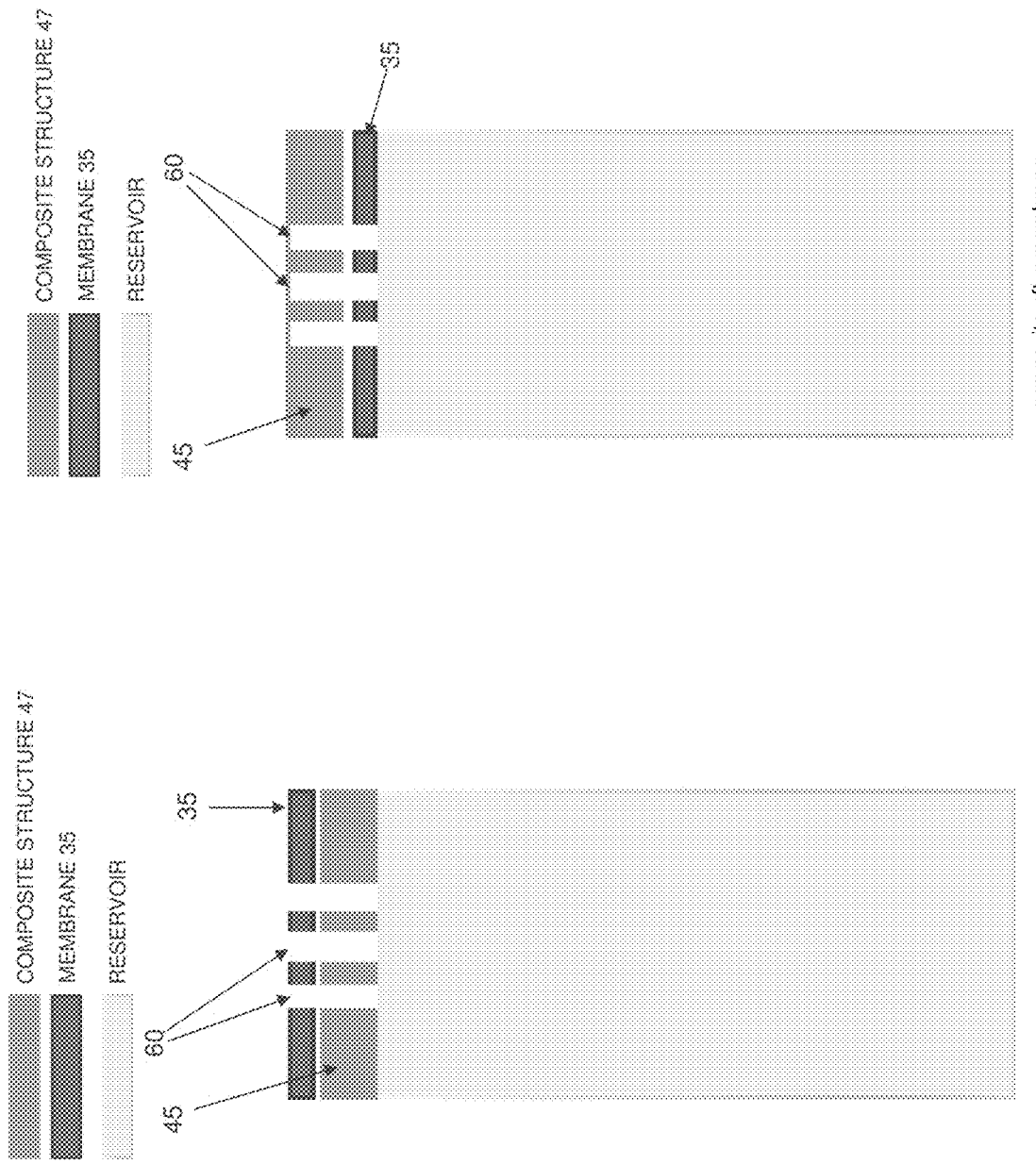

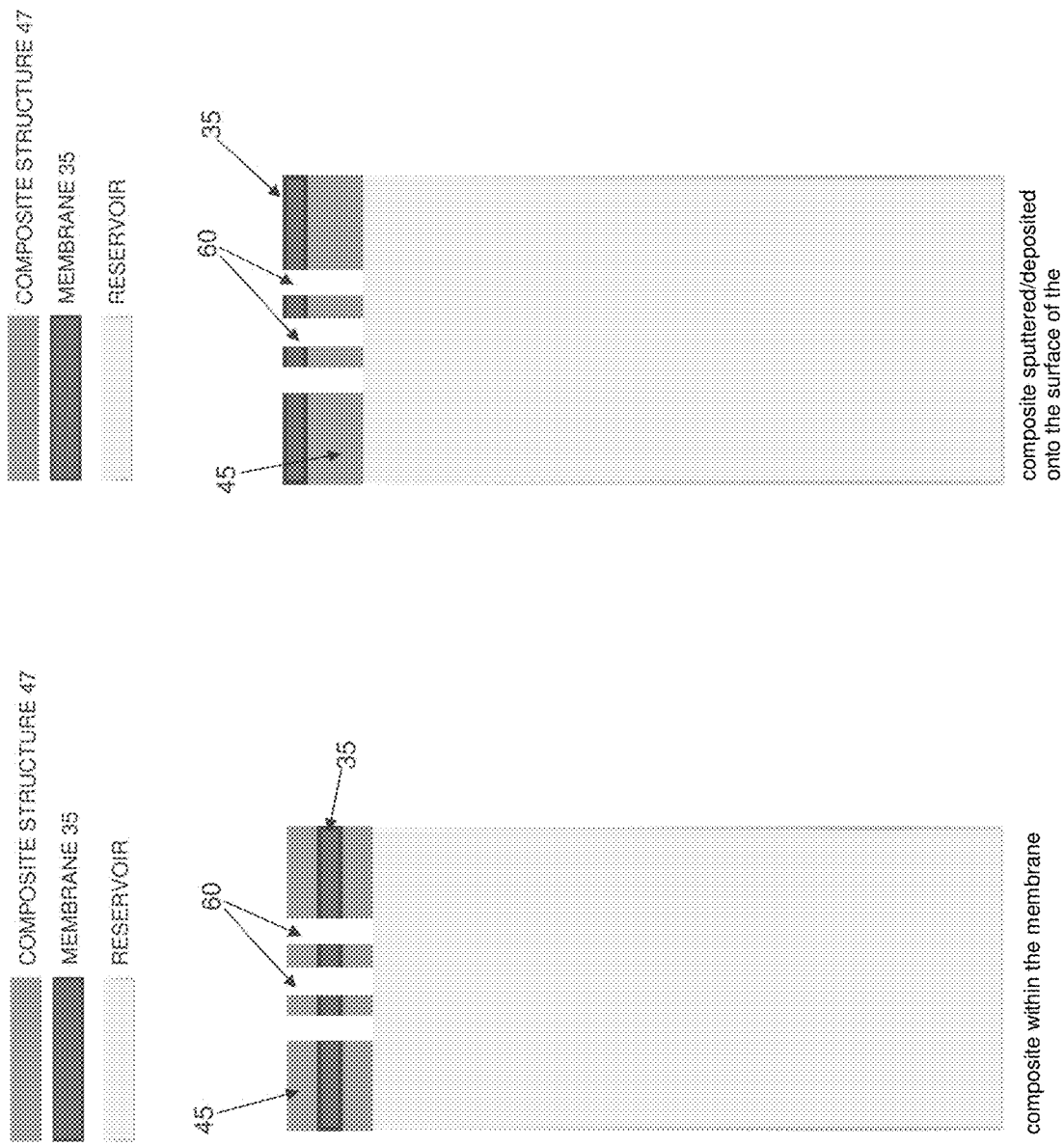

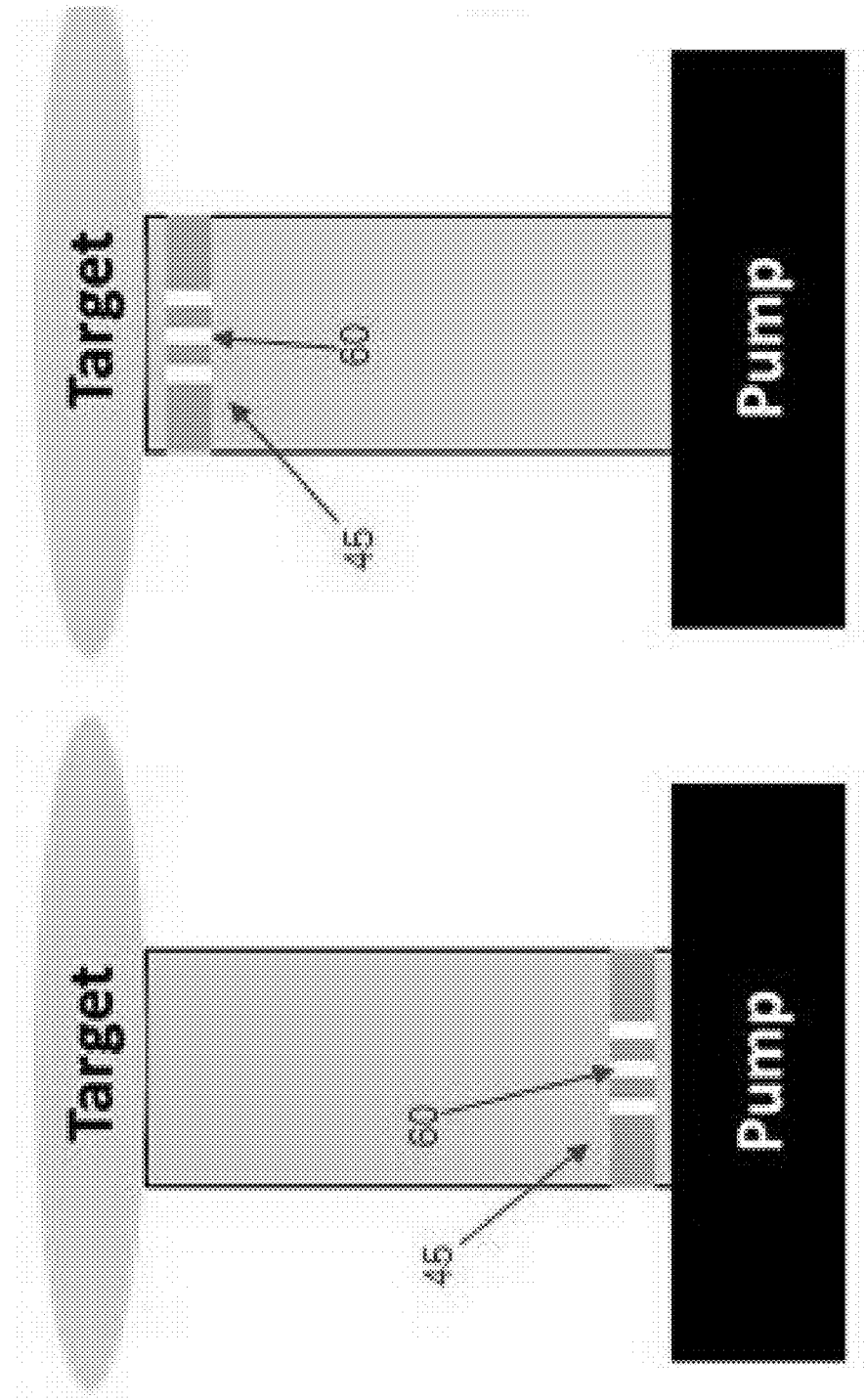
FIG. 6A — Composite at beginning of pathway
FIG. 6B — composite at end of fluid pathway

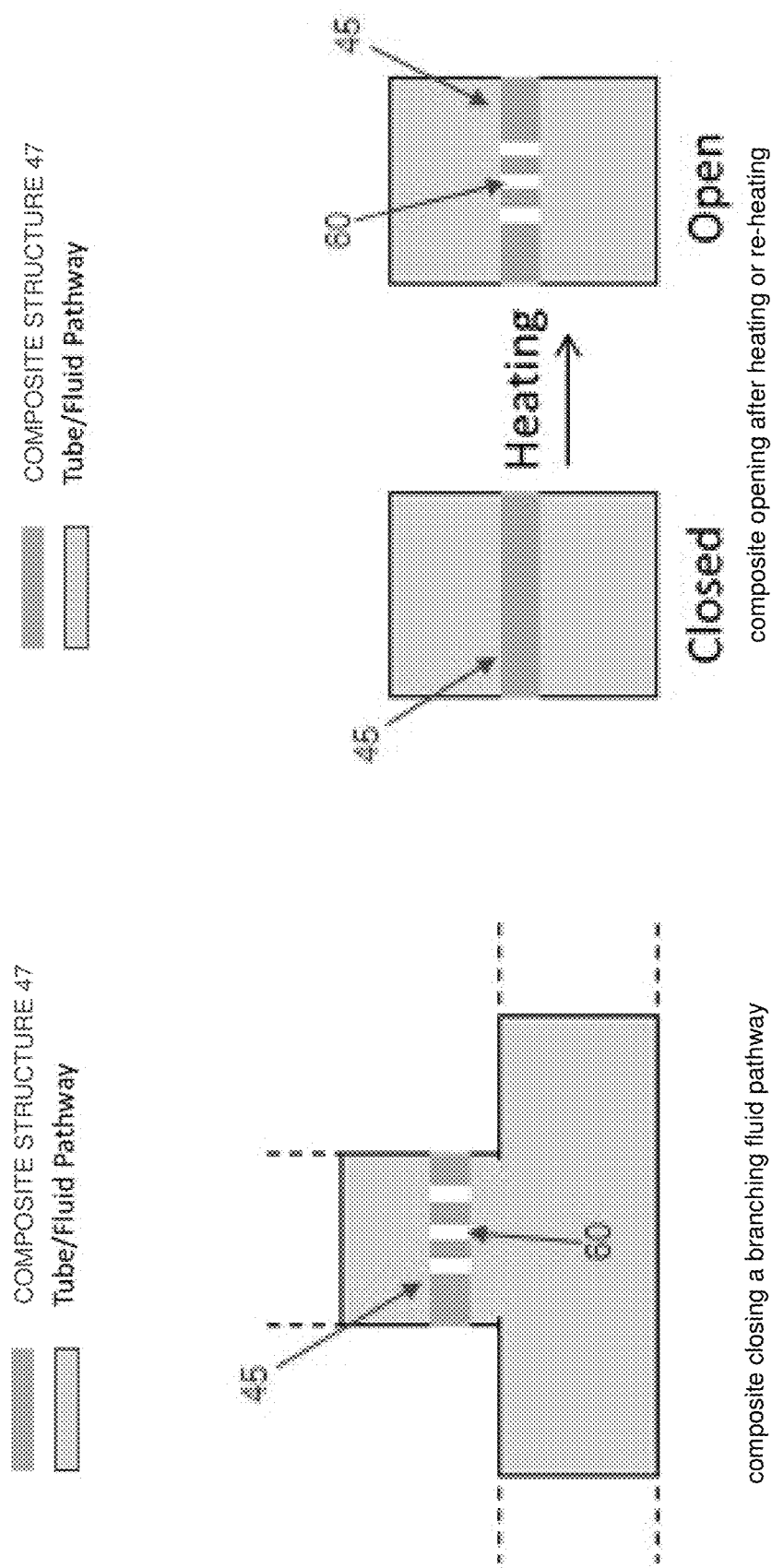

mesh immediately around holes second example mesh layout

Example mesh layout

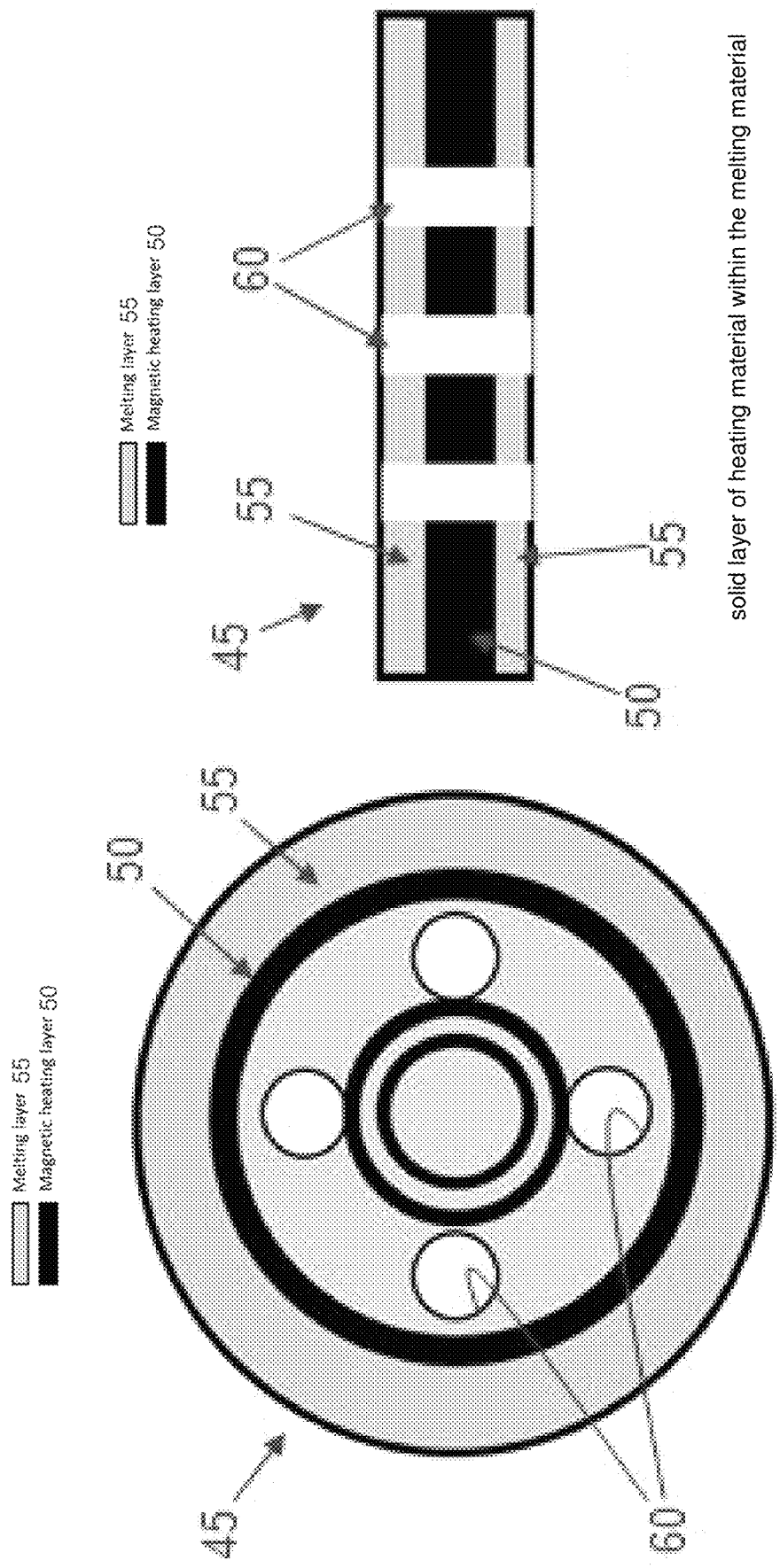

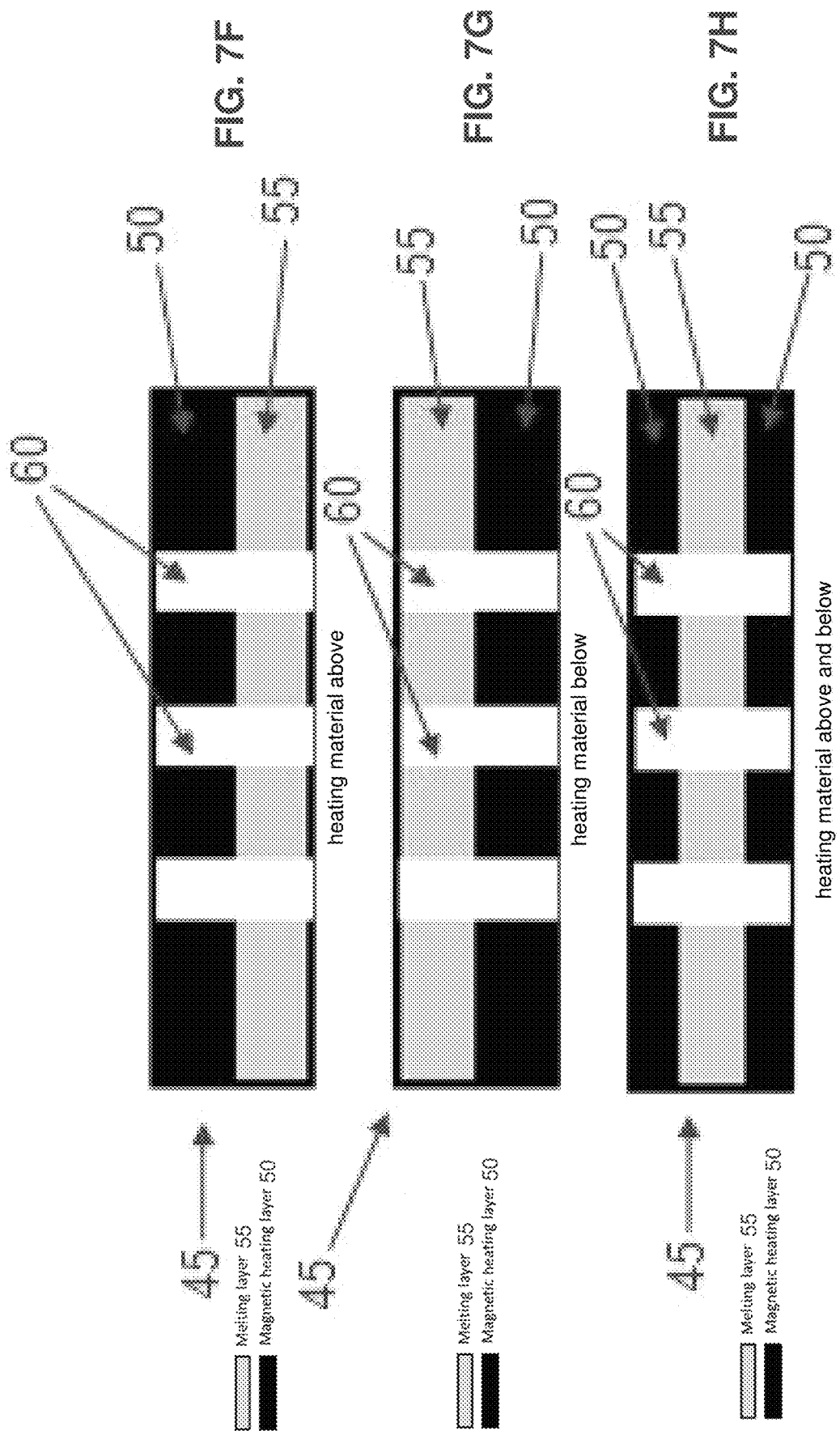

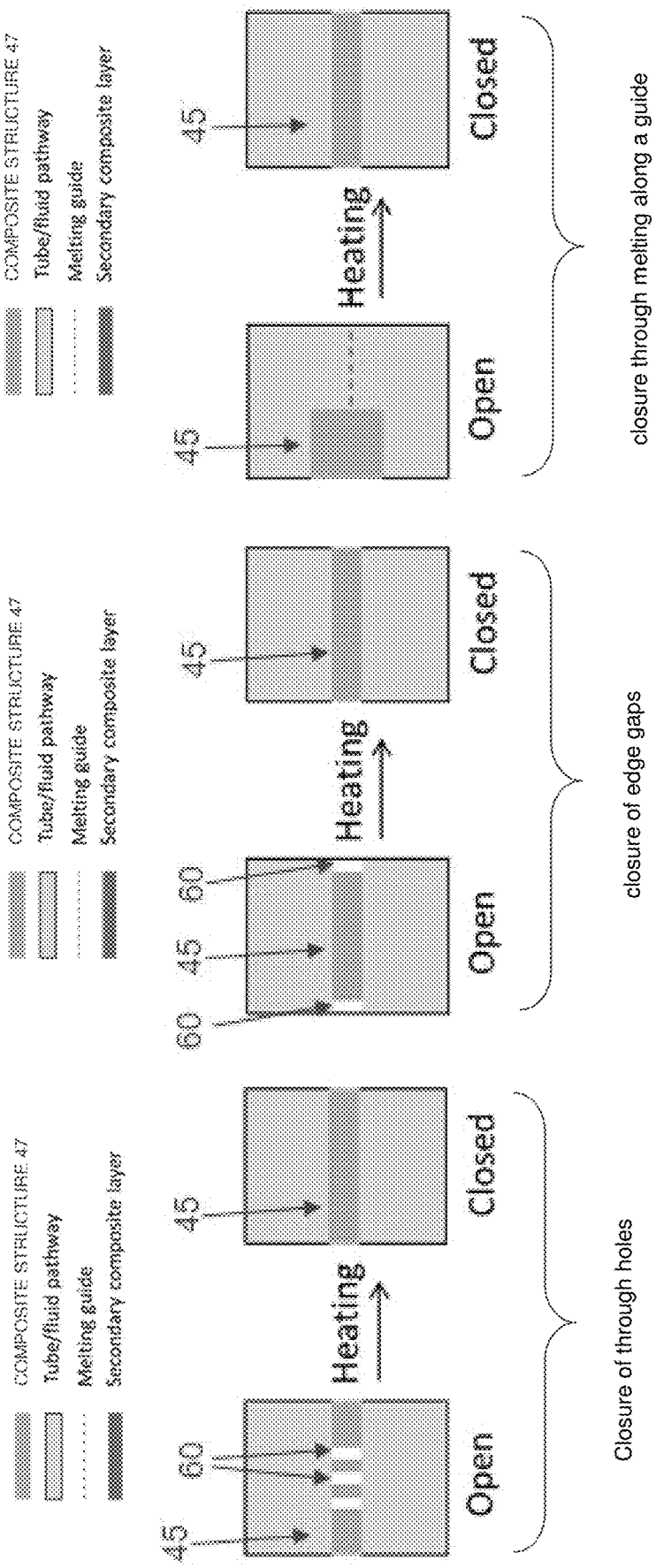

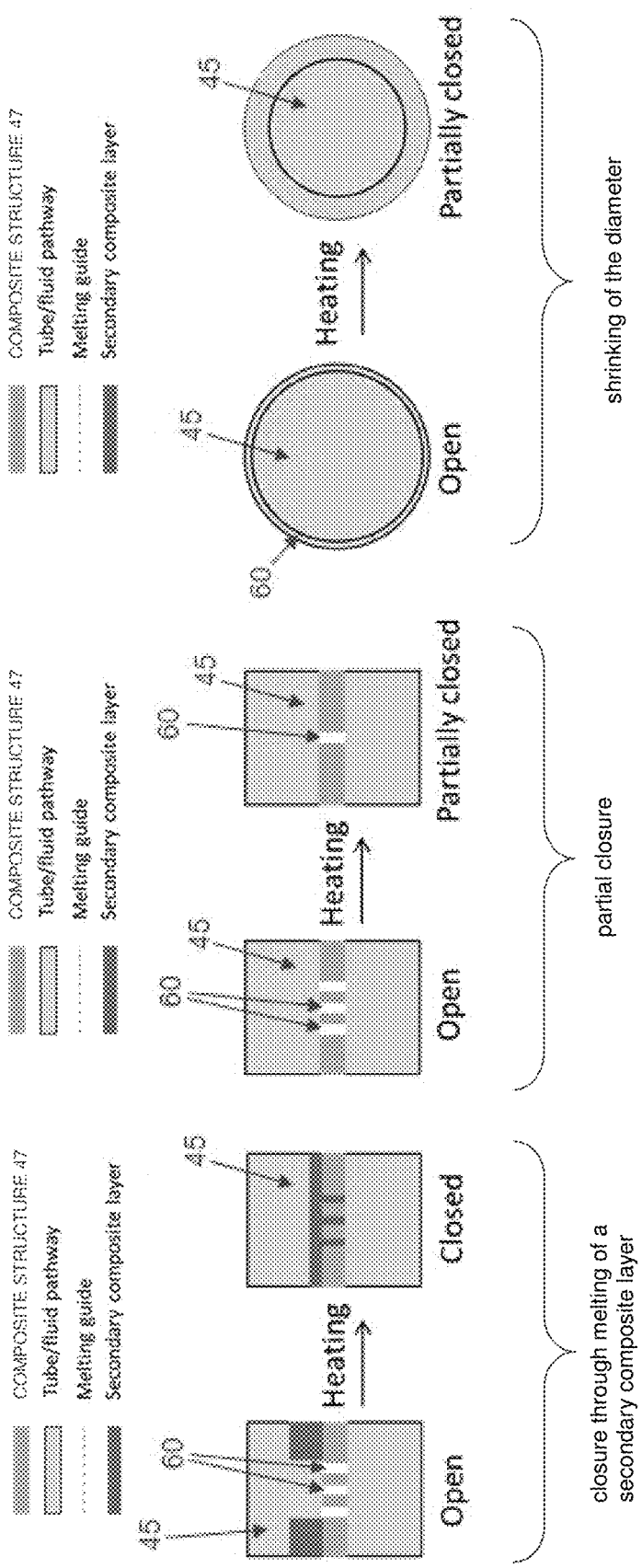

METHOD AND APPARATUS FOR THE FAIL-SAFE TERMINATION OF IN VIVO DRUG DELIVERY FROM AN IMPLANTABLE DRUG DELIVERY SYSTEM

REFERENCE TO PENDING PRIOR PATENT APPLICATIONS

This patent application is a continuation of prior U.S. patent application Ser. No. 15/769,401, filed Apr. 19, 2018 by The Methodist Hospital for METHOD AND APPARATUS FOR THE FAIL-SAFE TERMINATION OF IN VIVO DRUG DELIVERY FROM AN IMPLANTABLE DRUG DELIVERY SYSTEM, which patent application is a 371 national stage entry of prior International (PCT) Patent Application No. PCT/US16/57628, filed Oct. 19, 2016 by The Methodist Hospital for METHOD AND APPARATUS FOR THE FAIL-SAFE TERMINATION OF IN VIVO DRUG DELIVERY FROM AN IMPLANTABLE DRUG DELIVERY SYSTEM, which patent application in turn claims benefit of prior U.S. Provisional Patent Application Ser. No. 62/243,265, filed Oct. 19, 2015 by The Methodist Hospital for METHOD AND APPARATUS FOR THE FAIL-SAFE TERMINATION OF IN VIVO DRUG DELIVERY FROM AN IMPLANTABLE DRUG DELIVERY SYSTEM.

The three (3) above-identified patent applications are hereby incorporated herein by reference.

FIELD OF THE INVENTION

This invention relates to implantable drug delivery systems in general, and more particularly to methods and apparatus for the fail-safe termination of in vivo drug delivery from an implantable drug delivery system.

BACKGROUND OF THE INVENTION

Implantable drug delivery systems are well known in the art. Such implantable drug delivery systems are highly advantageous inasmuch as they can continuously release a given therapeutic drug and eliminate issues with patient compliance to a prescribed regimen. Furthermore, next-generation implantable drug delivery systems are enabling remote electronic control of drug delivery so as to provide telemedical treatment options to healthcare providers.

Unfortunately, current implantable drug delivery systems suffer from the disadvantage that, in the event that drug delivery must be terminated (e.g., due to an adverse patient reaction), and where the drug delivery system uses a passive release control (which is typical in the field) or where there is a malfunction of the electronic controller of the drug delivery system, etc., surgical explantation may be the only reliable option for terminating drug delivery. However, inasmuch as surgical explantation requires trained personnel, specialized and sterilized surgical equipment, and proper medical facilities, surgical explantation can be problematic, particularly in emergency situations.

Thus, there is need for a new method and apparatus for the rapid and effective termination of in vivo drug delivery from an implantable drug delivery system. The new method and apparatus should, ideally, allow minimally-trained personnel, or the patients themselves, to safely halt drug delivery until appropriate surgical explantation can be effected. The new method and apparatus should also, ideally, be activatable from outside the body and be fail-safe so as to ensure reliable termination of drug delivery when activated. Additionally, the new method and apparatus should be readily compatible with a wide range of drug delivery systems so as to facilitate widespread adoption of the technology.

SUMMARY OF THE INVENTION

The present invention comprises the provision and use of an implantable drug delivery system which comprises a housing having a reservoir for containing a drug, and a port for dispensing the drug to the patient. In accordance with the present invention, the implantable drug delivery system further comprises an emergency deactivation unit which normally passes the drug therethrough but which, upon the application of energy to the emergency deactivation unit, prevents the drug from passing through the emergency deactivation unit (and hence out of the implantable drug delivery system). In one preferred form of the invention, the emergency deactivation unit comprises a composite structure comprising a biocompatible ferromagnetic mesh and a meltable material. The meltable material normally has one or more holes therein which allow the drug to pass from the reservoir, through the composite structure, and out the port of the implantable drug delivery system. However, when a magnetic field is applied to the composite structure, a current is induced in the ferromagnetic mesh which heats the ferromagnetic mesh and melts the meltable material, thereby closing the hole(s) in the composite structure and blocking drug delivery to the patient.

Significantly, the emergency deactivation unit may be used with a wide range of drug delivery systems so as to facilitate widespread adoption of the technology. Furthermore, the emergency deactivation unit may be used to close substantially any implantable fluid pathway, including implantable fluid pathways used for devices other than drug delivery systems.

In one preferred form of the present invention, there is provided a method for the fail-safe termination of in vivo drug delivery from an implantable drug delivery system, the method comprising:
 providing an implantable drug delivery system comprising:
  a housing having a reservoir for containing a drug, and a port for dispensing the drug to a patient; and
  an emergency deactivation unit disposed between the reservoir and the port, the emergency deactivation unit comprising a composite structure comprising a biocompatible ferromagnetic mesh open to fluid flow and a hydrophobic meltable material, the hydrophobic meltable material comprising at least one hole therein for enabling a fluid to pass through the hydrophobic meltable material;
 implanting the implantable drug delivery system within a patient;
 enabling the drug to flow from the reservoir, through the at least one hole in the hydrophobic meltable material and out the port; and
 when drug flow is to be terminated, applying a magnetic field to the composite structure, such that a current is induced in the ferromagnetic mesh which heats the ferromagnetic mesh and melts the hydrophobic meltable material, thereby closing the at least one hole in the hydrophobic meltable material and blocking drug delivery to the patient.

In another preferred form of the present invention, there is provided apparatus for the fail-safe termination of in vivo drug delivery from an implantable drug delivery system, the apparatus comprising:

an implantable drug delivery system comprising:
  a housing having a reservoir for containing a drug, and a port for dispensing the drug to a patient; and
  an emergency deactivation unit disposed between the reservoir and the port, the emergency deactivation unit comprising a composite structure comprising a biocompatible ferromagnetic mesh open to fluid flow and a hydrophobic meltable material, the hydrophobic meltable material comprising at least one hole therein for enabling a fluid to pass through the hydrophobic meltable material;
  wherein, when an appropriate magnetic field is applied to the composite structure, a current is induced in the ferromagnetic mesh which heats the ferromagnetic mesh and melts the hydrophobic meltable material, thereby closing the at least one hole in the hydrophobic meltable material and blocking drug delivery to the patient.

In another preferred form of the present invention, there is provided a method for the fail-safe termination of fluid flow through a fluid pathway, the method comprising:
  providing an emergency deactivation unit comprising a composite structure comprising a biocompatible ferromagnetic mesh open to fluid flow and a hydrophobic meltable material, the hydrophobic meltable material comprising at least one hole therein for enabling a fluid to pass through the hydrophobic meltable material;
  positioning the emergency deactivation unit within a fluid pathway;
  enabling fluid to flow from one side of the emergency deactivation unit, through the at least one hole in the hydrophobic meltable material, to the other side of the emergency deactivation unit; and
  when fluid flow is to be terminated, applying a magnetic field to the composite structure, such that a current is induced in the ferromagnetic mesh which heats the ferromagnetic mesh and melts the hydrophobic meltable material, thereby closing the at least one hole in the hydrophobic meltable material and blocking fluid flow through the emergency deactivation unit.

In another preferred form of the present invention, there is provided apparatus for the fail-safe termination of fluid flow through a fluid pathway, the apparatus comprising:
  an emergency deactivation unit comprising a composite structure comprising a biocompatible ferromagnetic mesh open to fluid flow and a hydrophobic meltable material, the hydrophobic meltable material comprising at least one hole therein for enabling a fluid to pass through the hydrophobic meltable material;
  wherein, when an appropriate magnetic field is applied to the composite structure, a current is induced in the ferromagnetic mesh which heats the ferromagnetic mesh and melts the hydrophobic meltable material, thereby closing the at least one hole in the hydrophobic meltable material and blocking fluid flow through the emergency deactivation unit.

In another preferred form of the present invention, there is provided a method for the fail-safe termination of in vivo drug delivery from an implantable drug delivery system, the method comprising:
  providing an implantable drug delivery system comprising:
    a housing having a reservoir for containing a drug, and a port for dispensing the drug to a patient; and
    an emergency deactivation unit disposed between the reservoir and the port, the emergency deactivation unit comprising:
      a barrier element comprising hydrophobic material having a solid state at physiological temperature and a flowable state above physiological temperature, the barrier element comprising an opening extending therethrough for allowing fluid to pass through the barrier element; and
      a magnetic heating element adapted to increase in temperature when exposed to a magnetic field, the magnetic heating element being disposed adjacent to the opening;
  implanting the implantable drug delivery system within a patient;
  enabling the drug to flow from the reservoir, through the opening in the barrier element and out the port; and
  when drug flow is to be terminated, applying a magnetic field to the magnetic heating element, such that the temperature of the magnetic heating element increases, causing the hydrophobic material of the barrier element to flow, whereby to close the opening in the barrier element and block drug delivery to the patient.

In another preferred form of the present invention, there is provided apparatus for the fail-safe termination of in vivo drug delivery from an implantable drug delivery system, the apparatus comprising:
  an implantable drug delivery system comprising:
    a housing having a reservoir for containing a drug, and a port for dispensing the drug to a patient; and
    an emergency deactivation unit disposed between the reservoir and the port, the emergency deactivation unit comprising:
      a barrier element comprising hydrophobic material having a solid state at physiological temperature and a flowable state above physiological temperature, the barrier element comprising an opening extending therethrough for allowing fluid to pass through the barrier element; and
      a magnetic heating element adapted to increase in temperature when exposed to a magnetic field, the magnetic heating element being disposed adjacent to the opening;
      wherein, when an appropriate magnetic field is applied to the magnetic heating element, the temperature of the magnetic heating element increases, causing the hydrophobic material of the barrier element to flow, whereby to close the opening in the barrier element and block drug delivery to the patient.

In another preferred form of the present invention, there is provided a method for the fail-safe termination of fluid flow through a fluid pathway, the method comprising:
  providing an emergency deactivation unit comprising:
    a barrier element comprising a hydrophobic material having a solid state at physiological temperature and a flowable state above physiological temperature, the barrier element comprising an opening extending therethrough for allowing fluid to pass through the barrier element; and
    a magnetic heating element adapted to increase in temperature when exposed to a magnetic field, the magnetic heating element being disposed adjacent to the opening;
  positioning the emergency deactivation unit within the fluid pathway;
  enabling fluid to flow from one side of the emergency deactivation unit, through the opening in the barrier element, to the other side of the emergency deactivation unit; and when fluid flow is to be terminated, applying a magnetic field to the magnetic heating element, such that the temperature of the magnetic heating element increases, causing the hydrophobic material of the barrier element to flow, whereby to close the opening in the barrier element and block fluid flow through the emergency deactivation unit.

In another preferred form of the present invention, there is provided apparatus for the fail-safe termination of fluid flow through a fluid pathway, the apparatus comprising:

an emergency deactivation unit comprising:
- a barrier element comprising hydrophobic material having a solid state at physiological temperature and a flowable state above physiological temperature, the barrier element comprising an opening extending therethrough for allowing fluid to pass through the barrier element; and
- a magnetic heating element adapted to increase in temperature when exposed to a magnetic field, the magnetic heating element being disposed adjacent to the opening;

wherein, when an appropriate magnetic field is applied to the magnetic heating element, the temperature of the magnetic heating element increases, causing the hydrophobic material of the barrier element to flow, whereby to close the opening in the barrier element and block fluid flow through the emergency deactivation unit.

In another preferred form of the present invention, there is provided a method for the fail-safe termination of fluid flow through a fluid pathway, the method comprising:

providing an emergency deactivation unit comprising:
- a barrier element comprising a hydrophobic material having a solid state at physiological temperature and a flowable state above physiological temperature, the barrier element comprising an opening extending therethrough for allowing fluid to pass through the barrier element;

positioning the emergency deactivation unit within the fluid pathway;

enabling fluid to flow from one side of the emergency deactivation unit, through the opening in the barrier element, to the other side of the emergency deactivation unit; and when fluid flow is to be terminated, increasing the temperature of the barrier element, causing the hydrophobic material of the barrier element to flow, whereby to close the opening in the barrier element and block fluid flow through the emergency deactivation unit.

In another preferred form of the present invention, there is provided apparatus for the fail-safe termination of fluid flow through a fluid pathway, the apparatus comprising:

an emergency deactivation unit comprising:
- a barrier element comprising hydrophobic material having a solid state at physiological temperature and a flowable state above physiological temperature, the barrier element comprising an opening extending therethrough for allowing fluid to pass through the barrier element;

wherein appropriately increasing the temperature of the barrier element causes the hydrophobic material of the barrier element to flow, whereby to close the opening in the barrier element and block fluid flow through the emergency deactivation unit.

In another preferred form of the present invention, there is provided a method for manufacturing apparatus for the fail-safe termination of fluid flow through a fluid pathway, the method comprising:

providing a substrate comprising a hydrophobic material having a solid state at physiological temperature and a flowable state above physiological temperature;

positioning a heating element on the substrate;

positioning, atop the substrate and the heating element, a cover comprising a hydrophobic material having a solid state at physiological temperature and a flowable state above physiological temperature; and adhering the cover to the substrate and forming an opening through the cover and the substrate adjacent to the heating element.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 5A-5D are schematic views showing various dispositions of the emergency deactivation unit within the implantable drug delivery system;

FIGS. 6A-6D are schematic views showing various dispositions of an emergency deactivation unit within fluid passageways;

FIGS. 7A-7H are schematic views showing various configurations for the emergency deactivation unit; and FIGS. 8A-8G are schematic views showing operation of various configurations of the emergency deactivation unit.

DETAILED DESCRIPTION OF THE PREFERRED EMBODIMENTS

Implantable Drug Delivery System with Emergency Deactivation Unit

Figure 1B:
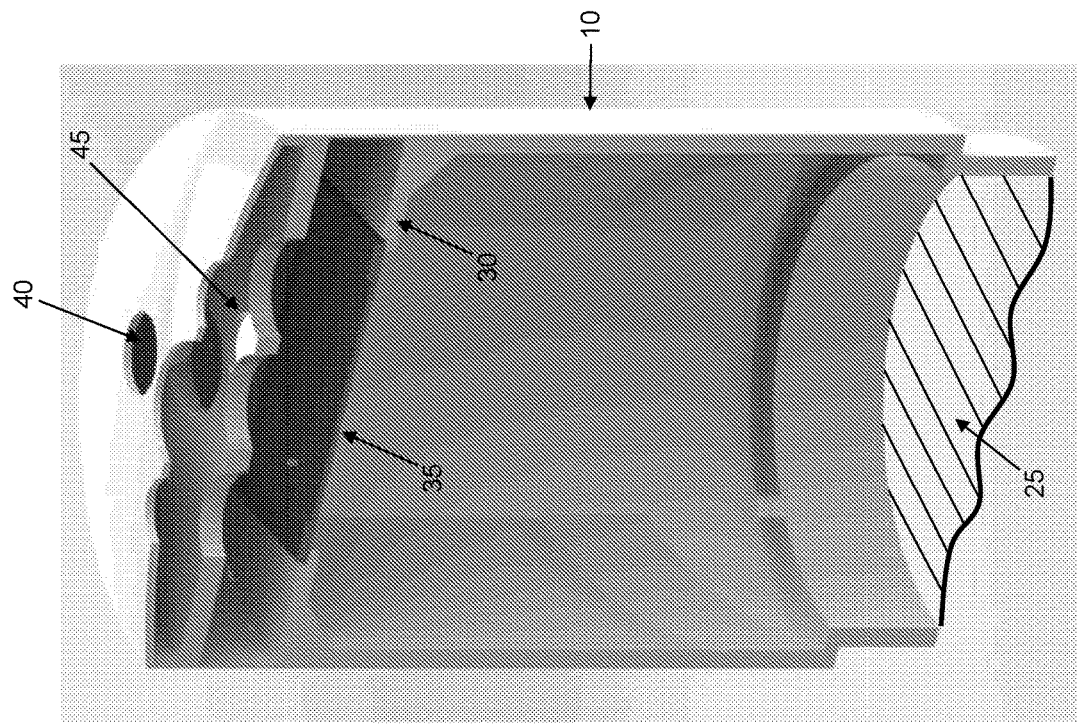
FIGS. 1A and 1B are schematic views showing an implantable drug delivery system with an emergency deactivation unit.
Figure 1A:
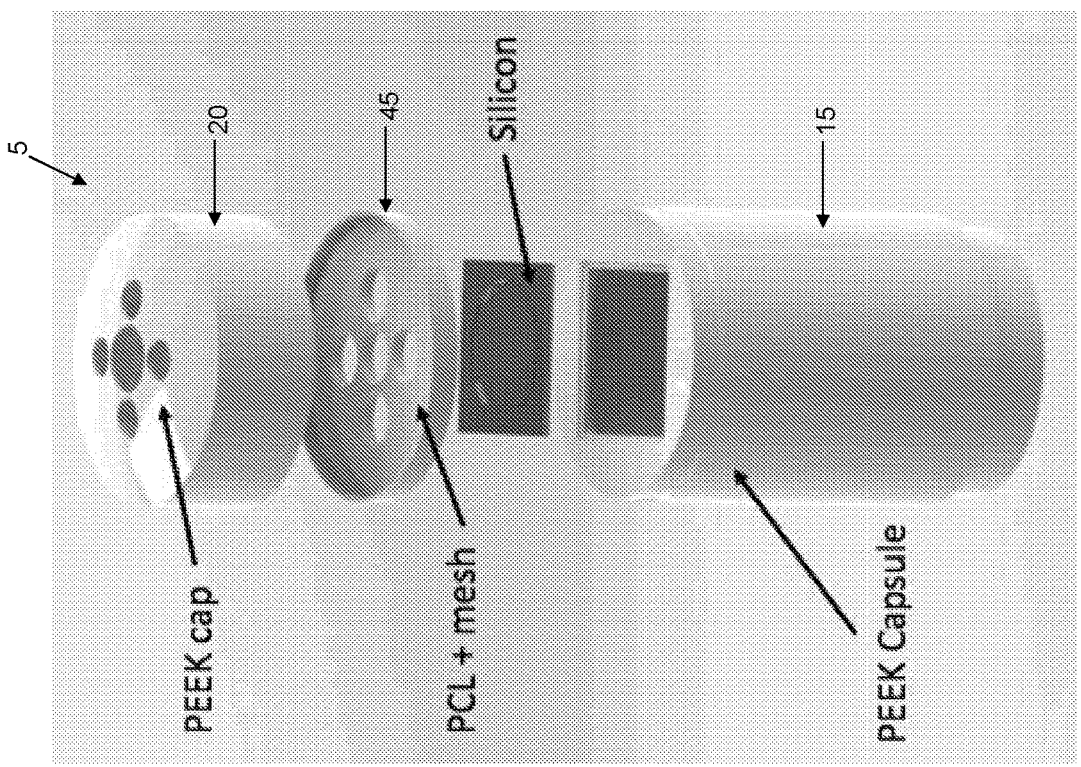
Figure 2B:
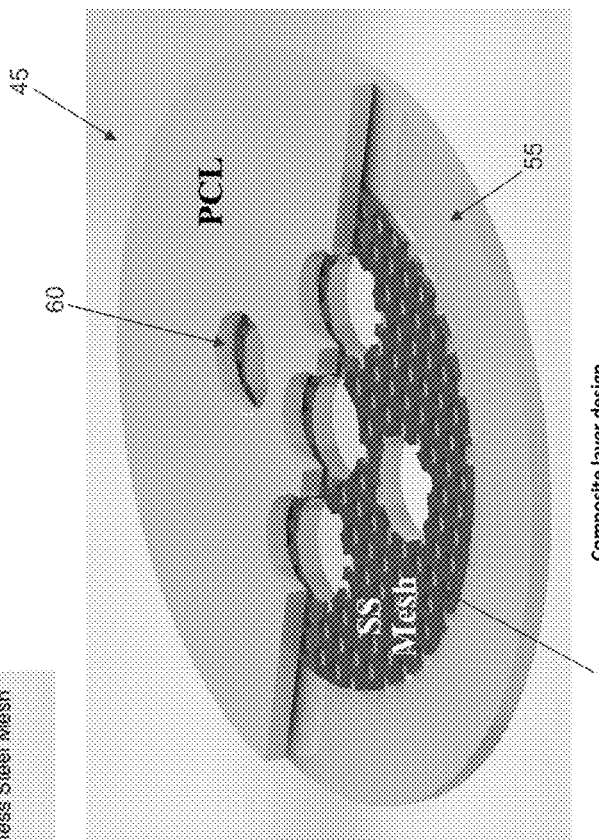
FIGS. 2A and 2B are schematic views showing the emergency deactivation unit incorporated in the implantable drug delivery system of FIGS. 1A and 1B.
Figure 2A:
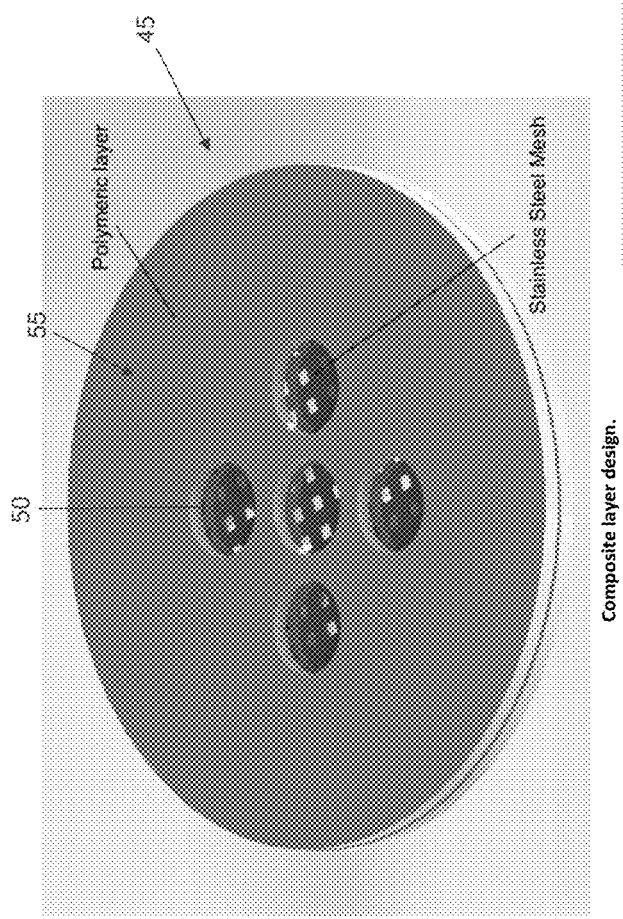
Figure 3:
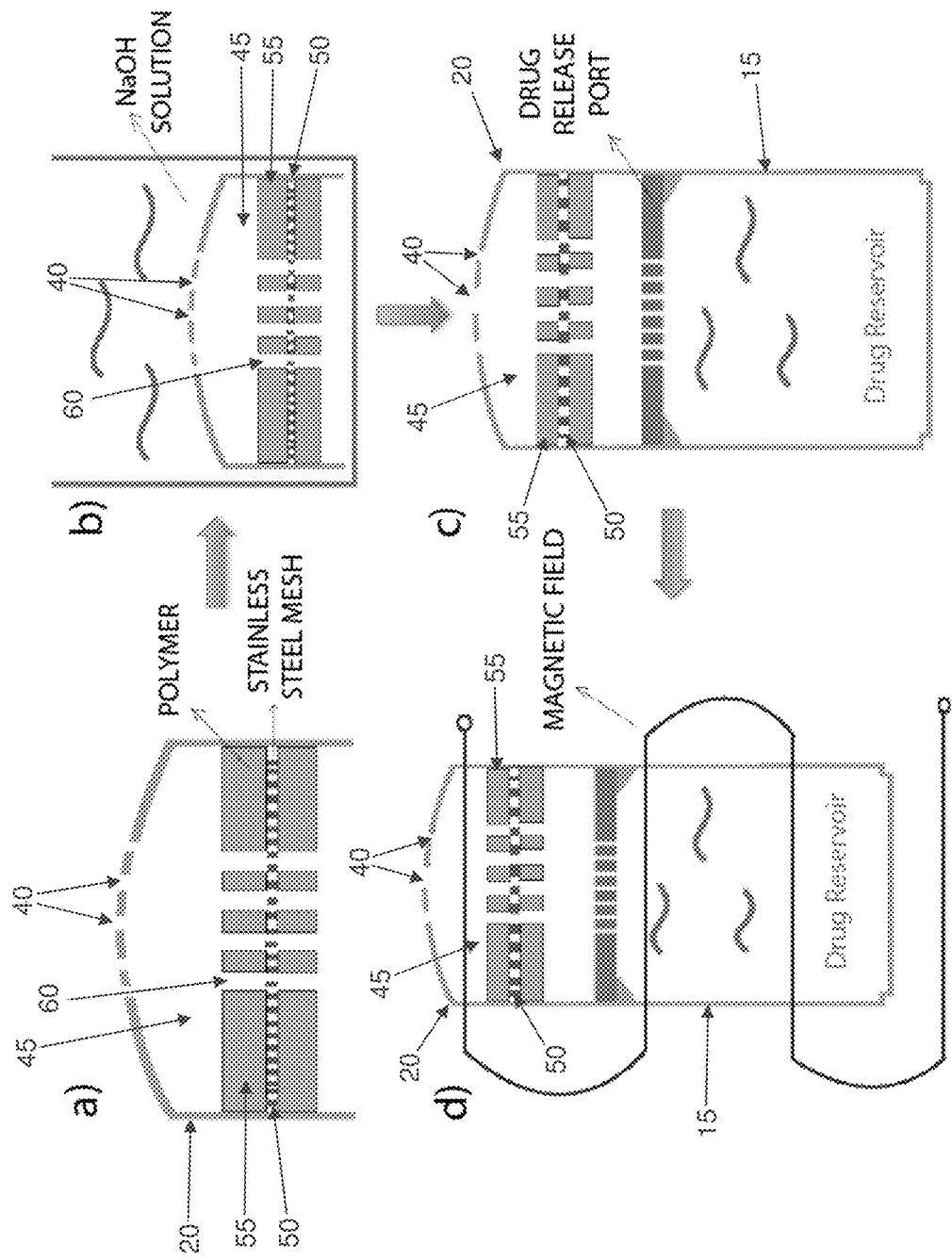
FIG. 3 is a schematic view showing assembly of the emergency deactivation unit within the implantable drug delivery system.

Looking first at FIGS. 1A and 1B, there is shown an implantable drug delivery system 5 (sometimes hereinafter referred to as the "nDS") formed in accordance with the present invention. Implantable drug delivery system 5 generally comprises a housing 10 comprising a body 15 and a cap 20. Body 15 may be cylindrical and is closed off at one end by an end wall 25. A flange 30 is formed at the other end of body 15, opposite end wall 25. Flange 30 supports a membrane 35 (e.g., a silicon membrane or other rate-limiting membrane) which regulates the release of a drug contained in body 15 between end wall 25 and flange 30/membrane 35. Cap 20 may have a similar cross-sectional profile to that of body 15, and fits on body 15, so as to cover flange 30/membrane 35. Cap 20 comprises one or more holes 40. As a result of this construction, a drug contained within body 15 between end wall 25 and flange 30/membrane 35 may be selectively released by membrane 35 so as to thereafter pass out of housing 10 through hole(s) 40.

In accordance with the present invention, and looking next at FIGS. 1A, 1B, 2A and 2B, implantable drug delivery system 5 also comprises an emergency deactivation unit 45 for the fail-safe termination of drug delivery from implantable drug delivery system 5. More particularly, emergency deactivation unit 45 generally comprises a composite structure 47 comprising a biocompatible ferromagnetic mesh 50 and a meltable material 55. Ferromagnetic mesh 50 comprises a biocompatible material which heats up when exposed to an appropriate magnetic field (i.e., a magnetic field below FDA limits) due to the creation of a current within the ferromagnetic mesh. In one preferred form of the invention, ferromagnetic mesh 50 comprises stainless steel. Meltable material 55 may be any biocompatible material which (i) is solid within normal physiological temperature ranges (e.g., 30-45 degrees C.), and (ii) melts at a slightly higher temperature (e.g., 50-70 degrees C.). In one preferred embodiment of the invention, meltable material 55 comprises a soft polymer such as polycaprolactone (PCL).

The ferromagnetic mesh 50 is overlaid with (and preferably encapsulated by) meltable material 55, and meltable material 55 includes one or more holes 60, so that fluid (e.g., a drug) can normally pass through composite structure 47 of emergency deactivation unit 45 by passing through hole(s) 60 and ferromagnetic mesh 50. However, when composite structure 47 of emergency deactivation unit 45 is exposed to an appropriate magnetic field, the magnetic field induces a current in ferromagnetic mesh 50 which, according to the Joule effect, will increase the temperature of the ferromagnetic mesh. The heated ferromagnetic mesh 50 then melts meltable material 55, causing hole(s) 60 to close, whereby to prevent fluid (e.g., a drug) from passing through composite structure 47 of emergency deactivation unit 45.

In accordance with the present invention, composite structure 47 of emergency deactivation unit 45 is mounted within cap 20 so that the composite structure of the emergency deactivation unit resides between membrane 35 and hole(s) 40. Alternatively, composite structure 47 of emergency deactivation unit 45 may be positioned at another location between the drug reservoir and hole(s) 40. As a result of this construction, when implantable drug delivery system 5 is implanted within a patient with a drug contained within body 15 between end wall 25 and flange 30/membrane 35, membrane 35 may release the drug from body 15 so that the drug flows through hole(s) 60 of composite structure 47 of emergency deactivation unit 45, and then through hole(s) 40 of cap 20, so that the drug is administered to the patient. However, if it should become necessary for drug delivery to be terminated (e.g., due to an adverse patient reaction or malfunction of the drug delivery system, etc.), an appropriate magnetic field is introduced to composite structure 47 of emergency deactivation unit 45 so that the magnetic field causes ferromagnetic mesh 50 to heat up, thereby melting meltable material 55, causing hole(s) 60 to close and thereby terminating drug delivery by implantable drug delivery system 5.

Thus, it will be seen that the present invention provides for the rapid and effective termination of in vivo drug delivery from an implantable drug delivery system. The present invention allows minimally-trained personnel, or the patients themselves, to safely halt drug delivery until appropriate surgical explantation can be effected. The present invention is also activatable from outside the body and is fail-safe so as to ensure termination of drug delivery when activated. Additionally, the present invention is readily compatible with a wide range of drug delivery systems so as to facilitate widespread adoption of the technology.

Example

1. Construction

By way of example but not limitation, in one exemplary form of the present invention, emergency deactivation unit 45 comprises a composite structure 47 formed out of a series of layers, i.e., a stainless steel (SS) ferromagnetic mesh 50 layer inside a polycaprolactone (PCL) meltable material 55 layer. The stainless steel ferromagnetic mesh 50 has a dimension of 10×10 mm, 150 μm thickness, and holes having a diameter of 300 μm. In this form of the invention, meltable material 55 is formed by solvent casting. More particularly, PCL (1 gr, 90 kDa) is dissolved in 5 ml of chloroform inside of a sealed bottle and agitated for 4 hours at room temperature (RT). After evaporating the chloroform (12 hours, RT), the PCL layer is dried at RT in a vacuum for 12 hours. Experiments have shown that untreated PCL is hydrophobic and does not allow for drug passage through holes 60 in meltable material 55. In order to increase the hydrophilicity of meltable material 55, the meltable material (i.e., the PCL) may be treated with a 2N NaOH solution for 4 hours prior to vacuum drying for an additional 2 hours. Once dry, two circular pieces of meltable material 55 (having a diameter of 12 mm) can be cut from the PCL. One layer of meltable material 55 is melted through heating with a hotplate for 1 minute at 80° C., and the stainless steel ferromagnetic mesh 50 is pressed into the meltable material 55 (i.e., into the liquid polymer). Maintaining the hotplate at the same temperature, a second layer of meltable material 55 (i.e., a second PCL layer) is placed on the top of the stainless steel ferromagnetic mesh 50. Compression during melting reduces the thickness of the final composite structure (made up of stainless steel ferromagnetic mesh 50 and meltable material 55) to a polymeric-metallic "sandwich" (i.e., the composite structure of emergency deactivation unit 45) having a thickness of about 700 μm. After cooling, five (5) through holes 60 (400 μm in diameter) are created symmetrically about the center of the meltable material 55. The composite emergency deactivation unit 45 is placed inside a polyether ether ketone (PEEK) implantable capsule (i.e., body 15) and adhered in place using a UV epoxy. A PEEK cap (i.e., cap 20) is placed over the composite layer (i.e., over emergency deactivation unit 45) at the top of the implantable capsule (i.e., at the top of body 25, just beyond the location of flange 30/membrane 35).

2. Emergency Deactivation

Figure 4:
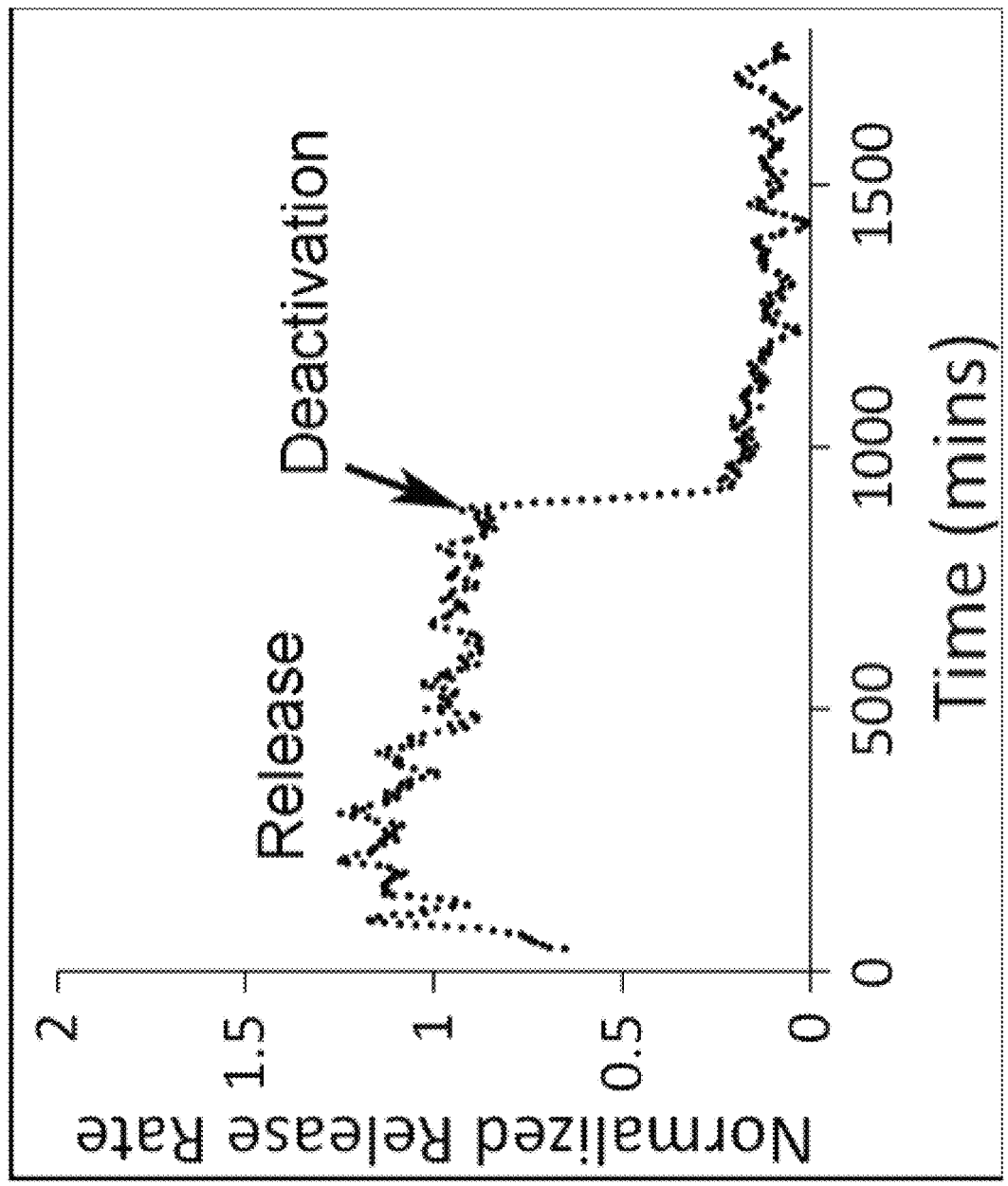
FIG. 4 is a schematic view showing normalized release data demonstrating deactivation of drug release.
Figure 7C:
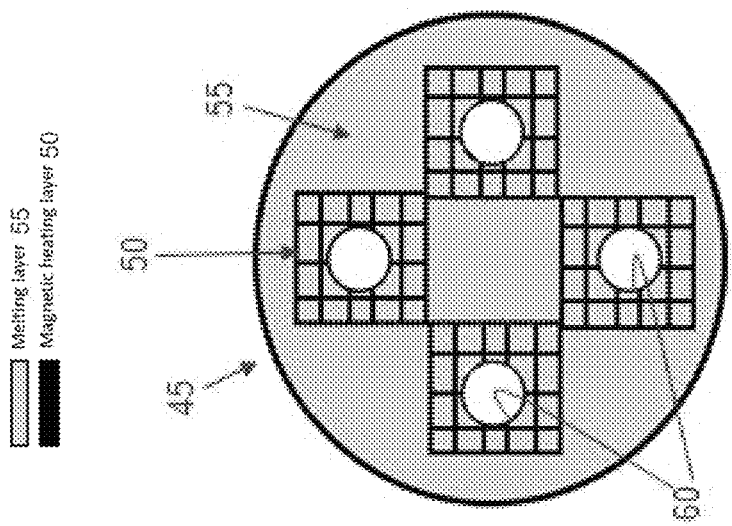
Figure 7B:
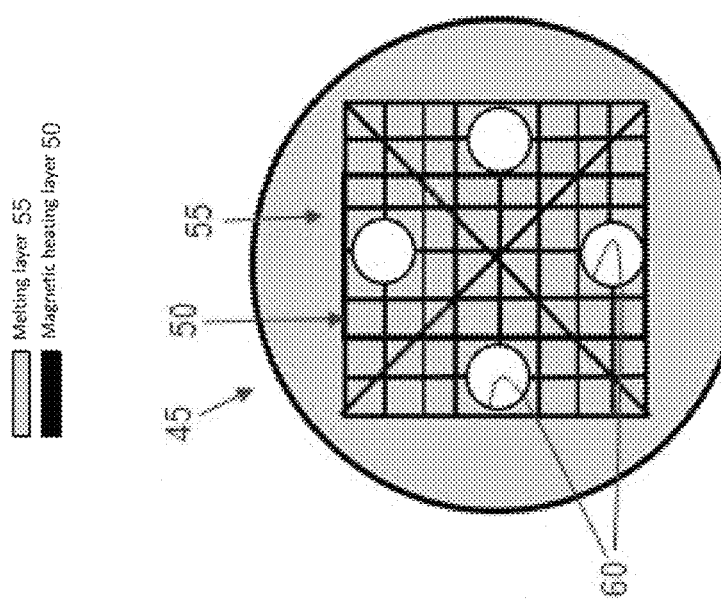
Figure 7A:
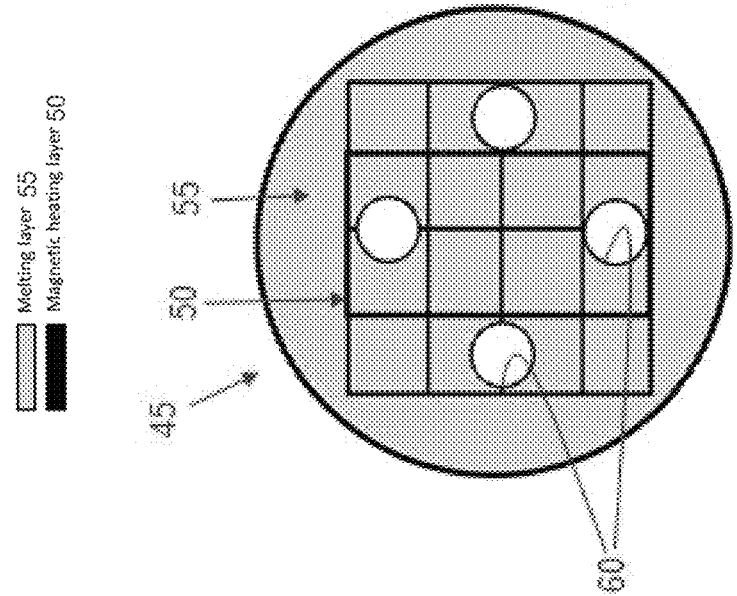
Figure 8D:
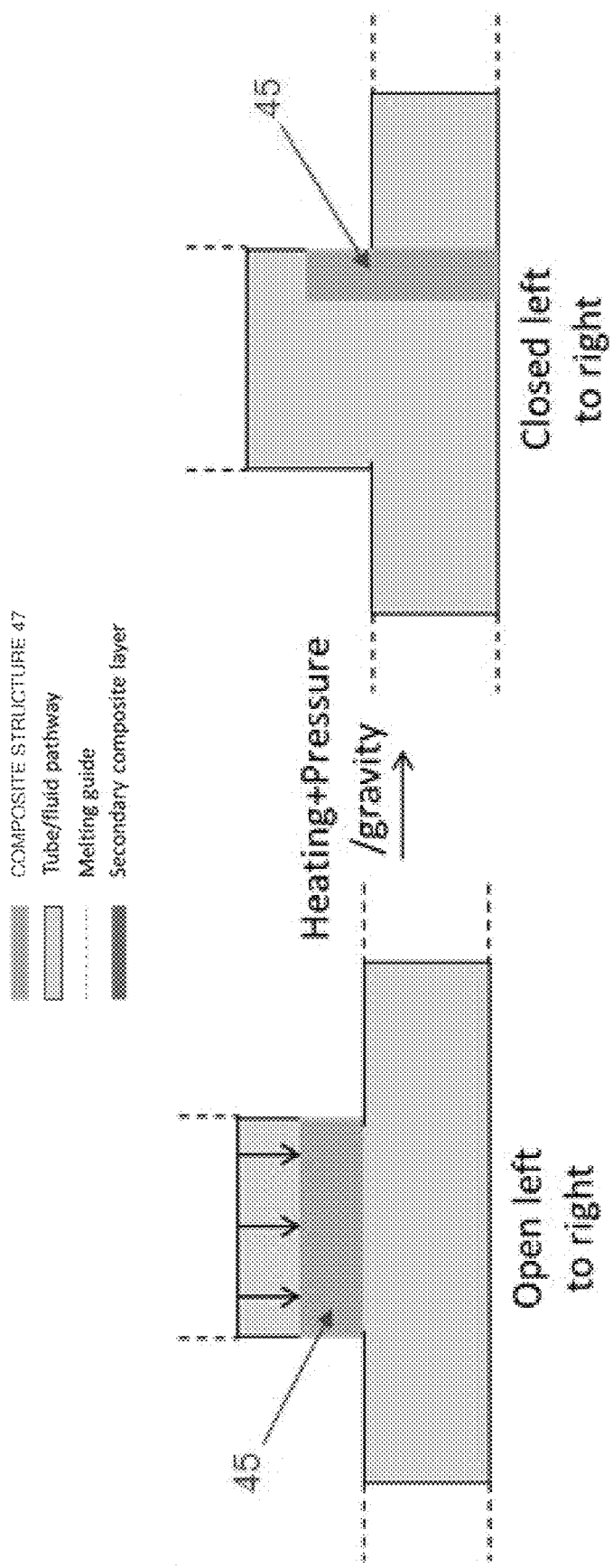

In order to test implantable drug delivery system 5, in one experiment, Rhodamine may be introduced in place of the drug contained in body 15 between end wall 25 and flange 30/membrane 35 body 15. After assembling the implantable drug delivery system 5, and in order to test the functioning of emergency deactivation unit 45, a custom spectroscopy cuvette having a volume of 13 ml was prepared. Implantable drug delivery system 5 was then placed perpendicular to the cuvette's cap and epoxied. A robotic, UV-Vis spectrophotometer was then used to collect absorbance measurements (545 nm) every minute for 16 hours. A stir bar (rotated at 1400 rpm) was placed at the bottom of the cuvette so as to maintain solution homogeneity. After 16 hours, implantable drug delivery system 5 was removed and placed in a 5 ml glass cuvette filled with 3 ml of water. The glass cuvette was placed within a magnetic field generator and a temperature sensor was placed inside the PEEK cap (i.e., inside cap 20). In order to simulate the temperature of the body (i.e., normal physiological temperature), the resting temperature was set to 37° C. Once implantable drug delivery system 5 reached the resting temperature, the magnetic field generator was activated, applying a magnetic field of 12 kA/m² for 1 minute and melting meltable material 55 (i.e., the PCL) of emergency deactivation unit 45 at about 50° C. After heating, the system was allowed to cool back to 37° C. A stereoscopic microscope was employed to inspect the emergency deactivation unit 45 (i.e., the PCL) and determine if the holes 60 were closed. After the RF (magnetic field) treatment, implantable drug delivery system 5 was replaced into the custom spectroscopy cuvette and the same solution as previously. UV-Vis absorbance measurements were taken every minute for another 16 hours. The release data (FIG. 4) demonstrates a 90% drop in normalized drug release.

Generalization of Inventive Concept

It is possible to generalize the inventive concept of the present invention to include other embodiments.

1. Placement of The Emergency Deactivation Unit Within an Implantable Drug Delivery System Or Within Devices Other Than Implantable Drug Delivery Systems The emergency deactivation unit may be placed in a variety of locations within an implantable drug delivery system or within devices other than implantable drug delivery systems.

By way of example but not limitation, and looking now at FIGS. 5A-5D, where emergency deactivation unit 45 is placed within an implantable drug delivery system 5, the emergency deactivation unit 45 may be placed:
   (i) on the outside of a release-limiting membrane (e.g., on the outside of membrane 35); or
   (ii) within the reservoir immediately before the membrane (e.g., between membrane 35 and end wall 25); or
   (iii) directly on or against the membrane (e.g., on either side of membrane 35); or
   (iv) sputtered/deposited onto the membrane itself (e.g., deposited directly on membrane 35).

By way of further example but not limitation, and looking now at FIGS. 6A-6D, where emergency deactivation unit 45 is placed within devices other than implantable drug delivery systems, the emergency deactivation unit 45 may be placed at the following locations in a general fluid pathway:
   (i) at the beginning of the fluid pathway; or
   (ii) at the end of the fluid pathway; or
   (iii) closing off a branching section of the fluid pathway.

Note that emergency deactivation unit 45 may be used to make a general fluid pathway more or less fluid tight, may receive additional heating to re-open one or more of the holes 60 in composite structure 47, and may be employed in pressurized or non-pressurized fluid pathways.

2. Composition of the Meltable Material

The meltable material (e.g., meltable material 55) may comprise any material which is solid at physiological temperatures and has a melting point somewhat higher than physiological temperatures (e.g., 5 degrees higher). By way of example but not limitation, the meltable material may comprise:
   (i) a polymer; or
   (ii) wax; or
   (iii) a shape memory alloy.

Note that the meltable material may be biodegradable or non-biodegradable, bioinert or non-bioinert.

Note also that the meltable material can be a singular material or a composite of meltable materials. Where the meltable material is a composite of meltable materials, the component materials can have the same melting point or can have differing melting points (e.g., to effect greater control over flow).

It should also be appreciated that the meltable material could be replaced by material which does not require melting, but instead uses other means (e.g., swelling) of closing the through holes (e.g., through holes 60).

3. Magnetic Heating Material

The magnetic heating material (e.g., ferromagnetic mesh 50) may be provided in a variety of configurations. By way of example but not limitation, and looking now at FIGS. 7A-7H, the magnetic heating material may be:
   (i) a mesh of different sizes; or
   (ii) a mesh limited to immediately around the through holes (e.g., through holes 60); or
   (iii) a single ring or multiple rings, either concentric or not; or
   (iv) any geometric shape allowing melt-based closure of the through holes; or
   (v) a single sheet within the meltable material; or
   (vi) a deposited layer on the meltable material (e.g., on top of, or below, or both).

Note that the magnetic heating material may also comprise ferromagnetic powder/shavings distributed throughout the meltable material.

The magnetic heating material (e.g., ferromagnetic mesh 50) may be formed out of a variety of materials. By way of example but not limitation, the magnetic heating material may comprise:
   (i) a ferromagnetic metal; or
   (ii) a paramagnetic material; or
   (iii) any material that will heat up in a magnetic field.

4. How Fluid Passage is Stopped

The emergency deactivation unit of the present invention may stop fluid flow in a variety of ways. By way of example but not limitation, and looking now at FIGS. 8A-8G, the emergency deactivation unit may stop fluid flow by:
   (i) closure of through holes 60 formed in composite structure 47; or
   (ii) sealing of composite structure 47 against fluid pathway surfaces; or
   (iii) running meltable material along a directed route to stop fluid flow through a pathway (either singular or branching)—the meltable material may be run along the directed route in a variety of ways (e.g., along a guide such as a mesh or struts, using gravity, utilizing layer placement, utilizing chemical properties, utilizing a pressure gradient in fluid, etc.).

Note that the through holes to be closed (e.g., through holes 60) can be in the same layer as the meltable material or can be in a secondary layer (into which the meltable material flows).

Note also that heating of the meltable material can be used to effect complete stopping of fluid flow or partial stopping of fluid flow.

MODIFICATIONS OF THE PREFERRED EMBODIMENTS

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for fail-safe termination of fluid flow through a fluid pathway, the method comprising:
   providing an emergency deactivation unit including a barrier element comprising a hydrophobic material having a solid state at physiological temperature and a flowable state above physiological temperature, the barrier element comprising an opening extending therethrough for allowing fluid to pass through the barrier element, and the barrier element comprising a heating element positioned to increase a temperature of the barrier element when activated;

positioning the emergency deactivation unit within the fluid pathway;

enabling fluid to flow from one side of the barrier element, through the opening in the barrier element, to the other side of the barrier element; and when fluid flow is to be terminated, increasing the temperature of the barrier element, causing the hydrophobic material of the barrier element to flow, whereby to close the opening in the barrier element and block fluid flow through the emergency deactivation unit.

2. The method according to claim 1, wherein increasing the temperature of the barrier element comprises applying energy to the barrier element from outside of the emergency deactivation unit.

3. The method according to claim 1, wherein increasing the temperature of the barrier element comprises applying a magnetic field to the barrier element.

4. The method according to claim 1, wherein the heating element is activated when exposed to a magnetic field.

5. The method according to claim 1, wherein the heating element is activated when external energy is applied thereto.

6. Apparatus for fail-safe termination of fluid flow through a fluid pathway, the apparatus comprising:

an emergency deactivation unit including a barrier element comprising a hydrophobic material having a solid state at physiological temperature and a flowable state above physiological temperature, the barrier element comprising an opening extending therethrough for allowing fluid to pass through the barrier element from a first side thereof to a second side thereof, and the barrier element comprising a heating element positioned to increase a temperature of the barrier element when activated;

wherein appropriately increasing the temperature of the barrier element causes the hydrophobic material of the barrier element to flow, whereby to close the opening in the barrier element and block fluid flow through the emergency deactivation unit.

7. The apparatus according to claim 6, wherein appropriately increasing the temperature of the barrier element comprises applying a magnetic field to the barrier element.

8. The apparatus according to claim 6, wherein the heating element is activated via a magnetic field.

9. The apparatus according to claim 6, comprising a cover proximate the emergency deactivation unit and defining a hole therethrough for allowing fluid to pass through the cover, wherein a space is defined between the cover and the emergency deactivation unit to separate the emergency deactivation unit from a physiological environment.

10. The apparatus according to claim 6, wherein the barrier element is biocompatible.

11. A method for manufacturing apparatus for fail-safe termination of fluid flow through a fluid pathway, the method comprising:

providing a substrate comprising a first hydrophobic material having a solid state at physiological temperature and a flowable state above physiological temperature;

positioning a heating element on the substrate;

positioning, atop the substrate and the heating element, a cover comprising a second hydrophobic material having a solid state at physiological temperature and a flowable state above physiological temperature; and adhering the cover to the substrate and forming an opening through the cover and the substrate adjacent to the heating element, such that the opening through the substrate is closable in response to activation of the heating element.

12. The method according to claim 11, wherein the first hydrophobic material and the second hydrophobic material both comprise polycaprolactone.

13. The method according to claim 11, wherein the heating element comprises a magnetic heating element adapted to increase in temperature when exposed to a magnetic field.

14. The method according to claim 13, wherein the magnetic heating element comprises a ferromagnetic mesh.

15. The method according to claim 11, wherein the opening is defined through the cover and the substrate to allow fluid to flow therethrough before activation of the heating element.

16. The method according to claim 11, wherein the heating element comprises a mesh aligned with and extending across the opening through the substrate.

17. The method according to claim 11, wherein the heating element is biocompatible.

* * * * *